United States Patent [19]

Pevarello et al.

[11] Patent Number: 5,912,242
[45] Date of Patent: Jun. 15, 1999

[54] N-(4-SUBSTITUTED-BENZYL)-2-AMINOLACTAM DERIVATIVES

[75] Inventors: Paolo Pevarello, Pavia; Raffaella Amici, Piacenza; Mario Varasi, Milan; Roberto Maj, Saronno; Patricia Salvati, Arese, all of Italy

[73] Assignee: Pharmacia & Upjohn S.p.A., Milan, Italy

[21] Appl. No.: 08/981,493

[22] PCT Filed: Jul. 5, 1996

[86] PCT No.: PCT/EP96/02962

§ 371 Date: Jan. 8, 1998

§ 102(e) Date: Jan. 8, 1998

[87] PCT Pub. No.: WO97/05111

PCT Pub. Date: Feb. 13, 1997

[30]   Foreign Application Priority Data

Jul. 27, 1995 [GB] United Kingdom .................. 9515411

[51] Int. Cl.$^6$ ................. A61K 31/395; C07D 205/085; C07D 207/26
[52] U.S. Cl. ............... 514/210; 514/212; 514/327; 514/424; 540/364; 540/527; 546/216; 548/550
[58] Field of Search ................ 548/550; 514/424, 514/327, 210, 212; 546/216; 540/364, 527

[56]   References Cited

FOREIGN PATENT DOCUMENTS 001 601   5/1979   European Pat. Off. .
171 159   2/1986   European Pat. Off. .
362 941   4/1990   European Pat. Off. .

*Primary Examiner*—Joseph K. McKane
*Attorney, Agent, or Firm*—Nikaido, Marmelstein, Murray & Oram LLP

[57]   ABSTRACT

The present invention relates to novel N-(4-substituted-benzyl)-2-aminolactams as therapeutic agents, pharmaceutical compositions and a process of preparation.

9 Claims, No Drawings

N-(4-SUBSTITUTED-BENZYL)-2-AMINOLACTAM DERIVATIVES

This application is a 371 of PCT/EP96/02962 filed Jul. 5, 1996.

The present invention relates to novel N-(4-substituted-benzyl)-2-aminolactams, to their use as therapeutic agents, to a process for their preparation and to pharmaceutically compositions containing them.

It has been found that novel N-(4-substituted-benzyl)-2-aminolactam derivatives as herein defined have valuable biological properties, in particular as antiepileptic, anti-Parkinson, neuroprotective, anti-depressant, antispastic and/or hypnotic agent.

The present invention provides novel compounds of formula (I)

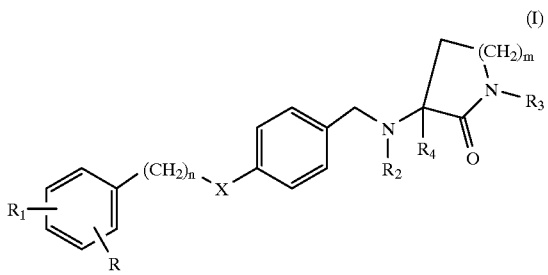

wherein:
m is zero, 1, 2 or 3;
n is zero, 1, 2 or 3;
X is —O—, —S—, —CH$_2$— or —NH—;
each of R and R$_1$ independently is hydrogen, C$_1$–C$_6$ alkyl, halogen, hydroxy, C$_1$–C$_4$ alkoxy or trifluoromethyl;
each of R$_2$, R$_3$ and R$_4$ independently is hydrogen, C$_1$–C$_6$ alkyl optionally substituted by a hydroxy group, or C$_3$–C$_7$ cycloalkyl;
and the pharmaceutically acceptable salts thereof.

The pharmaceutically acceptable salts of the compounds of formula (I) include acid addition salts with inorganic, e.g. hydrochloric, hydrobromic, sulphuric, and phosphoric acids, or organic, e.g. acetic, propionic, lactic, oxalic, malic, maleic, tartaric, citric, benzoic, mandelic, salicylic, C$_1$–C$_4$ alkylsulfonic and fumaric acids.

The compounds of the formula (I), their pharmaceutically acceptable salts may also form pharmaceutically acceptable solvates, such as hydrates, which are also object of the present invention.

The alkyl and alkoxy groups may be branched or straight groups.

A C$_1$–C$_6$ alkyl group is preferably a C$_1$–C$_4$ alkyl group, in particular methyl, ethyl, n- and iso-propyl, n-, iso-, sec- and tert-butyl, more preferably methyl or ethyl.

A C$_1$–C$_6$ alkyl group substituted by hydroxy is typically hydroxymethyl.

Representative examples of C$_1$–C$_4$ alkoxy groups include methoxy or ethoxy.

A halogen atom is e.g. chlorine, fluorine, bromine, in particular chlorine and fluorine, more preferably fluorine.

A C$_3$–C$_7$ cycloalkyl group is, for instance, a cyclopropyl, cyclohexyl or cycloheptyl group, in particular cyclopropyl.

The present invention also include within its scope both the metabolites and the pharmaceutically acceptable bio-precursors (otherwise known as pro-drugs) of the compounds of formula (I).

Compounds of formula (I) contain an asymmetric carbon atom and have optical l and d isomers. Accordingly, the invention includes all the possible isomers, in particular l and d isomers and their mixtures.

Preferred compounds of the invention are the compounds of formula (I) wherein
m is 1 or 2;
n is 1 or 2;
X is —O—, —S— or —NH—;
R is hydrogen;
R$_1$ is hydrogen or halogen;
each of R$_2$ and R$_4$ independently is hydrogen or C$_1$–C$_4$ alkyl;
R$_3$ is hydrogen or C$_1$–C$_4$ alkyl optionally substituted by a hydroxy group; and the pharmaceutically acceptable salts thereof.

More preferred compounds of the invention are the compounds of formula (I), wherein
m is 1;
n is 1;
X is —O— or —NH—;
R$_1$ is hydrogen or halogen;
R$_2$ is hydrogen or C$_1$–C$_4$ alkyl;
R$_3$ is hydrogen or C$_1$–C$_4$ alkyl optionally substituted by hydroxy;
R and R$_4$ are hydrogen; and the pharmaceutically acceptable salts thereof.

Examples of specific compounds of the invention are:
3-[4-(3-fluorobenzyloxy)benzylamino]-pyrrolidin-2-one;
3-[4-(3-chlorobenzyloxy)benzylamino]-pyrrolidin-2-one;
3-[4-(4-chlorobenzyloxy)benzylamino]-pyrrolidin-2-one;
3-[4-(3-bromobenzyloxy)benzylamino]-pyrrolidin-2-one;
3-[4-(4-fluorobenzyloxy)benzylamino]-pyrrolidin-2-one;
3-[4-(2-fluorobenzyloxy)benzylamino]-pyrrolidin-2-one;
3-[4-(3-fluorobenzyloxy)benzylamino]-azetidin-2-one;
3-[4-(3-fluorobenzyloxy)benzylamino]-piperidin-2-one;
3-[4-(3-fluorobenzyloxy)benzylamino]-azepan-2-one;
3-[4-(3-fluorobenzylamino)benzylamino]-pyrrolidin-2-one;
3-[4-(benzylsulfanyl)benzylamino]-pyrrolidin-2-one;
3-{[4-(3-fluorobenzyloxy)benzyl]methylamino}-pyrrolidin-2-one;
3-{[4-(3-fluorobenzyloxy)benzyl]methylamino}-1-hydroxymethyl-pyrrolidin-2-one;
3-[4-(3-fluorobenzyloxy)benzylamino]-1-methyl-pyrrolidin-2-one;
3-{[4-(3-chlorobenzyloxy)benzyl]methylamino}-pyrrolidin-2-one;
3-{[4-(3-bromobenzyloxy)benzyl]methylamino}-pyrrolidin-2-one,
if the case, either as a single isomer or as a mixture of isomers thereof, and the pharmaceutically acceptable salts thereof.

The compounds of the invention and the salts thereof can be obtained by a process comprising:
a) reaction of a compound of formula (II)

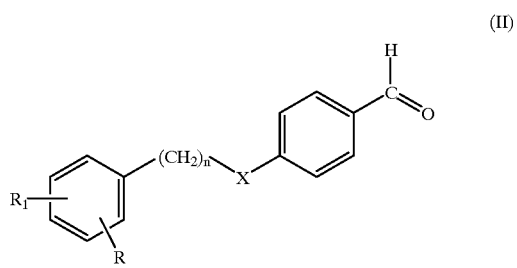

wherein n, R, R$_1$ and X are as defined above, with a compound of formula (III)

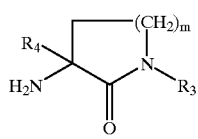

(III)

wherein m, $R_3$ and $R_4$ are as defined above, thus obtaining a compound of formula (I) in which $R_2$ is hydrogen; or b) reacting a compound of formula (IV)

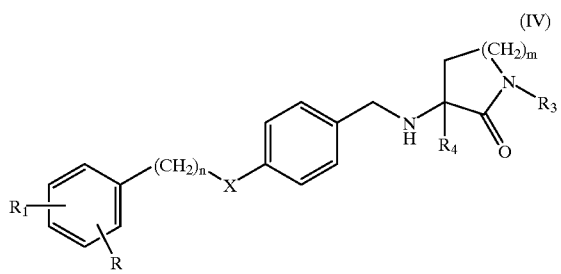

(IV)

wherein R, $R_1$, $R_3$, $R_4$, m, n and X are as defined above, with a compound of formula (V) or (VI)

(V)

(VI)

wherein W is a halogen atom; $R'_2$ is a $C_1$–$C_4$ alkyl and $R''_2$ is hydrogen or $C_1$–$C_3$ alkyl, thus obtaining a compound of the invention in which $R_2$ is $C_1$–$C_4$ alkyl; and, if desired, converting a compound of the invention into another compound of the invention and/or, if desired, converting a compound of the invention into a pharmaceutically acceptable salt and/or, if desired, converting a salt into a free compound and/or, if desired, separating a mixture of isomers of compounds of the invention into a single isomer.

All the processes described hereabove are analogy processes and can be carried out according to well known methods in organic chemistry.

A compound of formula (IV) is a compound of formula (I) in which $R_2$ is hydrogen.

The reaction of a compound of formula (II) with a compound of formula (III) to give a compound of formula (I) or (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride. Occasionally molecular sieves can be added to the reaction mixture for facilitating the reaction.

In a compound of formula (V) the halogen W is preferably iodine. The alkylation reaction of a compound of formula (IV) with a compound of formula (V) can be carried out in a suitable organic solvent, such as an alcohol, e.g. methanol, ethanol or isopropanol, in particular in ethanol, at a temperature ranging from about 0° C. to about 50° C.

The alkylation reaction of a compound of formula (IV) with an aldehyde of formula (VI) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

A compound of the invention can be converted, as stated above, into another compound of the invention by known methods. Process-variant b) above may be regarded as an example of optional conversion of a compound of the invention into another compound of the invention.

An isomer, e.g., a d- or l-isomer of a compound of the invention can be separately synthesized from optically pure starting material or separated from a racemate in a conventional manner.

Also the optional salification of a compound of the invention as well as the conversion of a salt into the free compound may be carried out by conventional methods.

When in the compounds of the present invention and in the intermediate-products thereof, groups are present, which need to be protected before submitting them to the hereabove illustrated reactions, they may be protected before being reacted and then deprotected according to methods well known in organic chemistry.

The compounds of formula (II), (III), (V) and (VI) are known compounds or can be obtained by known methods.

PHARMACOLOGY

The compounds of the invention are active on the central nervous system (CNS) and can be used in therapy, for example as antiepileptics, in the treatment of Parkinson's disease and as neuroprotective agents, e.g. preventing or treating neuronal loss associated with stroke, ischemia, CNS trauma, hypoglycaemia or surgery and in treating or preventing neurodegenerative diseases such as Alzheimer's disease, amyotrophic lateral sclerosis, Down's syndrome or Huntington's disease; they can also be used as antidepressants, hypnotics and antispastic agents. The activity on the CNS of the compounds of the invention was evaluated on the basis of pharmacological methods, such as, for example, the antagonism of convulsions and lethality induced by intravenous injection of bicuculline in mice (Antiepileptic Drugs, D. M. Woodbury et al. eds., 2nd-edition, Raven Press, New York, 1982), or the antagonism of maximal electroshock seizures (MES) (Woodbury, L. A. and Davenport, V. D., Arch. Int. Pharmacodyn. Ther. 92; 97–104, 1952).

A representative group of compounds of the invention was tested in the MES test as described before and found to be active as reported in Table 1 below.

TABLE 1

| Compound | MES ED$_{50}$ |
| --- | --- |
| FCE 28861 | 23.7 |
| FCE 29530 | 27.1 |
| FCE 29487A | 30.1 |
| FCE 28860A | 20.8 |
| FCE 29481A | 10.4 |
| FCE 29483A | 9.95 |
| FCE 29495A | 27.6 |
| FCE 29532A | 43.0 |
| FCE 29531 | 27.3 |
| FCE 29642A | 9.82 |
| FCE 29643 | 40.2 |
| FCE 29646A | 24.2 |
| FCE 29823A | 15.6 |
| FCE 29821A | 13.77 |

A patient is treated according to the present invention by a method comprising administering to the patient an effective amount of one of the compounds of the invention. In this way the present compounds can be used to treat disorders of the central nervous system, for example epilepsy or Parkinson's disease; or as neuroprotective agents, anti-depressants, hypnotics or anti-spastic agents. The condition of a patient may thus be improved.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans e.g. for the representative compound of the invention 3-[4-(3-chlorobenzyloxy)benzylamino]-pyrrolidin-2-one may range from about 1 to about 500 mg pro dose, from 1 to 5 times daily.

The invention includes pharmaceutical compositions comprising a compound of the invention in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspension.

The syrups may contain as carrier, for example, saccharose or saccharose with glycerine and/or mannitol and/or sorbitol.

The suspension and the emulsion may contain as carrier, for example, a natural gum, agar, sodium alginate, pectin, methylcellulose, carboxymethylcellulose, or polyvinyl alcohol.

The suspension or solutions for intramuscolar injections may contain, together with the active compound, a pharmaceutically acceptable carrier, e.g. sterile water, olive oil, ethyl oleate, glycols, e.g. propylene glycol, and, if desidered, a suitable amount of lidocaine hydrochloride. The solutions for intravenous injections or infusion may contain as carrier, for example, sterile water or preferably they may be in the form of sterile, acqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

(S)-3-[4-(3-fluorobenzyloxy)benzylamino]-pyrrolidin-2-one, methanesulfonate

To a solution of (S)-3-amino-2-pyrrolidinone hydrochloride (Synthesis, 1978, 614) (2.0 g; 0.0146 mol) in anhydrous methanol (60 ml), under stirring and nitrogen, 2.0 g of 3 Å molecular sieves were added and then, in a single portion, NaBH$_3$CN (0.77 g; 0.0122 mol); after 10 minutes, 3.4 g (0.0148 mol) of 4-(3-fluorobenzyloxy)benzaldeyde were added, in 40 ml of anhydrous methanol. After three hours the reaction was completed, the mixture filtered, the solution was evaporated to give a residue which was directly flash-chromatographed on silica gel (eluent: CHCl$_3$ 97: CH$_3$OH 3: 30% NH$_4$OH 0.3) to give a white solid (3.4 g; 74%). The free base thus obtained was treated with a stoichiometric amount of methanesulfonic acid to yield the title compound (m.p. 140.5–143.5° C; $[\alpha]_D^{25}$+35.2 (c=1.22, AcOH).

Analogously the following products can be obtained, starting from the corresponding aldehyde and the appropriate 3-aminolactam:

(S)-3-[4-(3-chlorobenzyloxy)benzylamino]-pyrrolidin-2-one, methanesulfonate:
  m.p. 138–144° C.; $[\alpha]_D^{25}$=–32.6 (c=1.2, ACOH);
(S)-3-[4-(3-fluorobenzyloxy)benzylamino]-piperidin-2-one:
  m.p. 98–101° C.; $[\alpha]_D^{25}$=–3.7 (c=1.0, ACOH);
(S)-3-[4-(3-bromobenzyloxy)benzylamino]-pyrrolidin-2-one, methanesulfonate:
  m.p. 138.5–143.5° C.; $[\alpha]_D^{25}$=–30.0 (c=1, ACOH);
(S)-3-[4-(4-fluorobenzyloxy)benzylamino]-pyrrolidin-2-one, methanesulfonate:
  m.p. 141° C.; $[\alpha]_D^{25}$=–34.4 (c=1.2, ACOH);
(S)-3-[4-(4-chlorobenzyloxy)benzylamino]-pyrrolidin-2-one:
  m.p. 172–176° C.; $[\alpha]_D^{25}$=–35.0 (c=1, ACOH);
(S)-3-[4-(2-fluorobenzyloxy)benzylamino]-pyrrolidin-2-one, methanesulfonate:
  m.p. 176.5–179° C.; $[\alpha]_D^{25}$=–34.0 (c=1, ACOH);
3-[4-(3-fluorobenzyloxy)benzylamino]-azetidin-2-one:
  m.p. 89–91° C. (dec.);
(S)-3-[4-(3-fluorobenzyloxy)benzylamino]-azepan-2-one, methanesulfonate:
  m.p. 214–217.5° C.; $[\alpha]_D^{25}$=–13.1 (c=1, H$_2$O);
(S)-3-[4-(3-fluorobenzylamino)benzylamino]-pyrrolidin-2-one, dihydrochloride:
  m.p. 165° C.; $[\alpha]_D^{25}$=–30.3 (c=1, ACOH);
(S)-3-[4-(benzylsulfanyl)benzylamino]-pyrrolidin-2-one, methanesulfonate:
  m.p. 138° C. (dec.); $[\alpha]_D^{25}$=–37.2 (c=1.1, ACOH);
3-[4-(3-fluorobenzyloxy)benzylamino]-3-methyl-pyrrolidin-2-one, methanesulfonate; and
(S)-3-[4-(3-fluorobenzyloxy)benzylamino]-1-methyl-pyrrolidin-2-one, hydrochloride:
  m.p. 168–170° C.; $[\alpha]_D^{25}$=–31.6 (c=1.2, NCOH).

EXAMPLE 2

(S)-3-{[4-(3-fluorobenzyloxy)benzyl]methylamino}-pyrrolidin-2-one

One g (0.00318 mol) of (S)-3-[4-(3-fluorobenzyloxy)benzylamino]pyrrolidin-2-one was dissolved in acetonitrile (50 ml) under a nitrogen stream. To this mixture, 1.6 ml (0.0196 mol) of 37% formaldehyde and 0.29 g (0.00460 mol) of sodium cyanoborohydride were added at room temperature. After 20 minutes, glacial acetic acid was dropped up to neutrality of the solution. The mixture was stirred for 40 minutes and was evaporated to dryness. 40 ml of 2 N KOH were added to the residue. After extracting with ethyl acetate, washing with N/2 KOH and then with water and brine, the organic layer was dried on $Na_2SO_4$, then filtered and evaporated to obtain a residue which was flash-chromatographed on silica gel (eluant: $CHCl_3$ 200: $CH_3OH$ 3: 30% $NH_4OH$ 0.2) to give 0.73 g (70%) of a white solid.

m.p. 89–92° C.; $[\alpha]_D^{25}=-39.8$ (c=1.1, ACOH).

Analogously the following products can be prepared starting from the corresponding secondary amine:

3-{[4-(3-chlorobenzyloxy)benzyl]methylamino}-pyrrolidin-2-one; and

3-{[4-(3-bromobenzyloxy)benzyl]methylamino}-pyrrolidin-2-one.

EXAMPLE 3

(S)-(+)-3-{[4-(3-fluorobenzyloxy)benzyl]methylamino}-1-hydroxymethyl-pyrrolidin-2-one To a stirred solution of 1.45 g (0.00461 mol) of (S)-3-[4-(3-fluorobenzyloxy)benzylamino]pyrrolidin-2-one and 3.7 ml (0.0493 mol) of 40% aqueous formaldehyde in 70 ml of acetonitrile was added 0.36 g (0.00573 mol) of sodium cyanoborohydride. The reaction mixture was stirred for 20 min, and then glacial acetic acid was added dropwise up to neutrality of the solution. Stirring was continued for an additional 40 min, the solvent was evaporated at reduced pressure, and 40 ml of 0.5 N NaOH was added to the residue. After extracting with ethyl acetate and washing with brine, the organic layer was dried on $Na_2SO_4$, then filtered and evaporated to obtain a residue which was flash-chromatographed on silica gel (eluant: $CHCl_3$ 90: MeOH 10) to give an oil. Treatment of the oil thus obtained with di-isopropyl ether afforded the title compound as a white solid (0.95 g; 57%).

m.p. 96–98° C.; $[\alpha]_D^{25}=+2.4$ (c=1.18, MeOH).

EXAMPLE 4

With the usual methods of pharmaceutical technique, preparation can be made of capsules having the following composition:

| | |
|---|---|
| (S)-3-[4-(3-chlorobenzyloxy)benzylamino]-pyrrolidin-2-one, methanesulfonate | 50 mg |
| Talc powder | 2 mg |
| Corn starch | 2 mg |
| Microcrystalline cellulose | 6 mg |
| Magnesium stearate | 1 mg |

We claim:

1. A compound of formula (I)

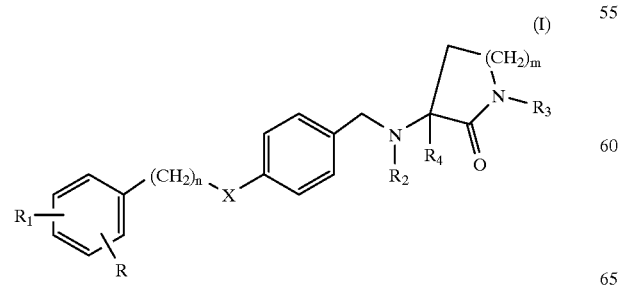

(I)

wherein:

m is zero, 1, 2 or 3;

n is zero, 1, 2 or 3;

X is —O—, —S—, —$CH_2$— or —NH—;

each of R and $R_1$ independently is hydrogen, $C_1$–$C_6$ alkyl, halogen, hydroxy, $C_1$–$C_4$ alkoxy or trifluoromethyl;

each of $R_2$, $R_3$ and $R_4$ independently is hydrogen, $C_1$–$C_6$ alkyl optionally substituted by a hydroxy group, or $C_3$–$C_7$ cycloalkyl;

or a pharmaceutically acceptable salt thereof.

2. A compound of formula (I), according to claim 1, wherein:

m is 1 or 2;

n is 1 or 2;

X is —O—, —S—or —NH—;

R is hydrogen;

$R_1$ is hydrogen or halogen;

each of $R_2$ and $R_4$ independently is hydrogen or $C_1$–$C_4$ alkyl;

$R_3$ is hydrogen or $C_1$–$C_4$ alkyl optionally substituted by a hydroxy group;

or a pharmaceutically acceptable salt thereof.

3. A compound of formula (I), according to claim 1, wherein:

m is 1;

n is 1;

X is —O— or —NH—;

$R_1$ is hydrogen or halogen $R_2$ is hydrogen or $C_1$–$C_4$ alkyl;

$R_3$ is hydrogen or $C_1$–$C_4$ alkyl optionally substituted by hydroxy;

R and $R_4$ are hydrogen;

or a pharmaceutically acceptable salt thereof.

4. A process for the preparation of a compound of formula (I), as defined in claim 1, or a pharmaceutically acceptable salt thereof, the process comprising:

a) reaction of a compound of formula (II)

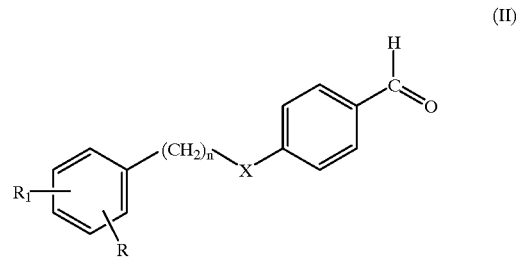

(II)

wherein n, R, $R_1$ and X are as defined in claim 1, with a compound of formula (III)

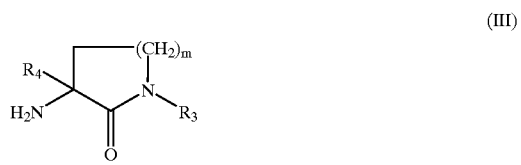

(III)

wherein m, $R_3$ and $R_4$ are as defined in claim 1, thus obtaining a compound of formula (I) in which $R_2$ is hydrogen; or b) reacting a compound of formula (IV)

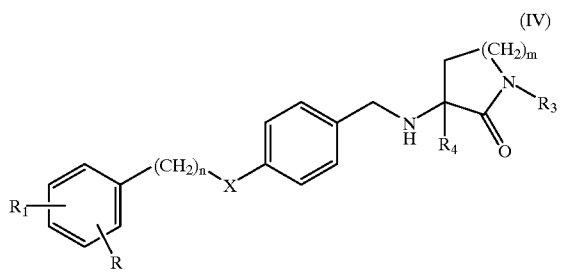

wherein R, $R_1$, $R_3$, $R_4$, m, n and X are as defined in claim 1, with a compound of formula (V) or (VI)

$R'_2 W$ (V)

$R''_2 CHO$ (VI)

wherein W is a halogen atom; $R'_2$ is a $C_1$–$C_4$ alkyl and $R''_2$ is hydrogen or $C_1$–$C_3$ alkyl, thus obtaining a compound of the invention in which $R_2$ is $C_1$–$C_4$ alkyl; and, if desired, converting a compound of the invention into another compound of the invention and/or, if desired, converting a compound of the invention into a pharmaceutically acceptable salt and/or, if desired, converting a salt into a free compound and/or, if desired, separating a mixture of isomers of compounds of the invention into a single isomer.

5. A pharmaceutical composition comprising a suitable carrier and/or diluent and, as an active principle, a compound of formula (I), as defined in claim 1, or a pharmaceutically acceptable salt thereof.

6. A compound of formula (I), as defined in claim 1, or a pharmaceutically acceptable salt thereof, for use as an active therapeutic substance.

7. A compound of formula (I), as defined in claim 1, or a pharmaceutically acceptable salt thereof, for use as antiepileptic, anti-Parkinson, neuroprotective, anti-depressant, antispastic and hypnotic agent, and in treating neurodegenerative diseases.

8. A method of treating a neurodegenerative disease in a patient in need of such treatment, comprising administering to said patient a neurodegenerative disease treating effective amount of a compound of claim 1.

9. A compound selected from the group consisting of:

3-[4-(3-fluorobenzyloxy)benzylamino]-pyrrolidin-2-one;

3-[4-(3-chlorobenzyloxy)benzylamino]-pyrrolidin-2-one;

3-[4-(4-chlorobenzyloxy)benzylamino]-pyrrolidin-2-one;

3-[4-(3-bromobenzyloxy)benzylamino]-pyrrolidin-2-one;

3-[4-(4-fluorobenzyloxy)benzylamino]-pyrrolidin-2-one;

3-[4-(2-fluorobenzyloxy)benzylamino]-pyrrolidin-2-one;

3-[4-(3-fluorobenzyloxy)benzylamino]-azetidin-2-one;

3-[4-(3-fluorobenzyloxy)benzylamino]-piperidin-2-one;

4-[4-(3-fluorobenzyloxy)benzylamino]-azepan-2-one;

3-[4-(3-fluorobenzylamino)benzylamino]-pyrrolidin-2-one;

3-[4-(benzylsulfanyl)benzylamino]-pyrrolidin-2-one;

3-{[4-(3-fluorobenzyloxy)benzyl]methylamino}-pyrrolidin-2-one;

3-{[4-(3-fluorobenzyloxy)benzyl]methylamino}-1-hydroxymethyl-pyrrolidin-2-one;

3-[4-(3-fluorobenzyloxy)benzylamino]-1-methyl-pyrrolidin-2-one;

3-{[4-(3-chlorobenzyloxy)benzyl]methylamino}-pyrrolidin-2-one;

3-{[4-(3-bromobenzyloxy)benzyl]methylamino}-pyrrolidin-2-one, if the case, either as a single isomer or as a mixture of isomers thereof, and the pharmaceutically acceptable salts thereof.

* * * * *